United States Patent
Hwang

(10) Patent No.: US 6,443,915 B1
(45) Date of Patent: Sep. 3, 2002

(54) CONTROL DEVICE AND METHOD OF PORTABLE SKIN BEAUTIFYING APPARATUS

(76) Inventor: Hyun-Bae Hwang, 451-17 Eunam-dong, Puk-gu, Kwangju (KR)

( * ) Notice: Subject to any disclaimer, the term of this patent is extended or adjusted under 35 U.S.C. 154(b) by 0 days.

(21) Appl. No.: 09/454,746

(22) Filed: Dec. 6, 1999

(30) Foreign Application Priority Data

Dec. 7, 1998 (KR) .................................. 53396/1998

(51) Int. Cl.⁷ .................................................. A61H 1/00
(52) U.S. Cl. ............................ 601/15; 601/18; 601/21; 601/70; 601/72
(58) Field of Search ........................... 601/15, 18, 19, 601/20, 21, 67, 69, 70, 72, 80; 128/898

(56) References Cited

U.S. PATENT DOCUMENTS

| | | | | |
|---|---|---|---|---|
| 4,010,742 A | * | 3/1977 | Kim ........................... | 128/24.4 |
| 5,010,896 A | * | 4/1991 | Westbrook .................. | 128/798 |
| 5,086,788 A | * | 2/1992 | Castel et al. ................ | 128/800 |
| 5,336,159 A | * | 8/1994 | Cheng ......................... | 601/15 |
| 6,007,502 A | * | 12/1999 | Lee .............................. | 601/17 |
| 6,119,038 A | * | 9/2000 | Cook ............................ | 607/3 |

* cited by examiner

*Primary Examiner*—Michael A. Brown
*Assistant Examiner*—Benjamin K. Koo

(57) ABSTRACT

Disclosed are a control method and device of a portable beautifying apparatus capable of being easily moved, beautifying the human face skin by galvanic ion current, far infrared ray, and vibration, and measuring the skin state. The control device includes: a microcomputer for controlling the whole operation of the beautifying apparatus; a key input part for inputting into the microcomputer an operation command selected by s user; a galvanic ion current output part for elevating a battery's power to a level and outputting galvanic ion current according to the control of the microcomputer; a galvanic ion current detecting part for determining whether or not the galvanic ion current output from the galvanic ion current output part flows onto the user's face skin; a vibration generating part for generating a vibration according to the control of the microcomputer; and a far-infrared ray generating part for generating a far-infrared ray according to the control of the microcomputer.

9 Claims, 14 Drawing Sheets

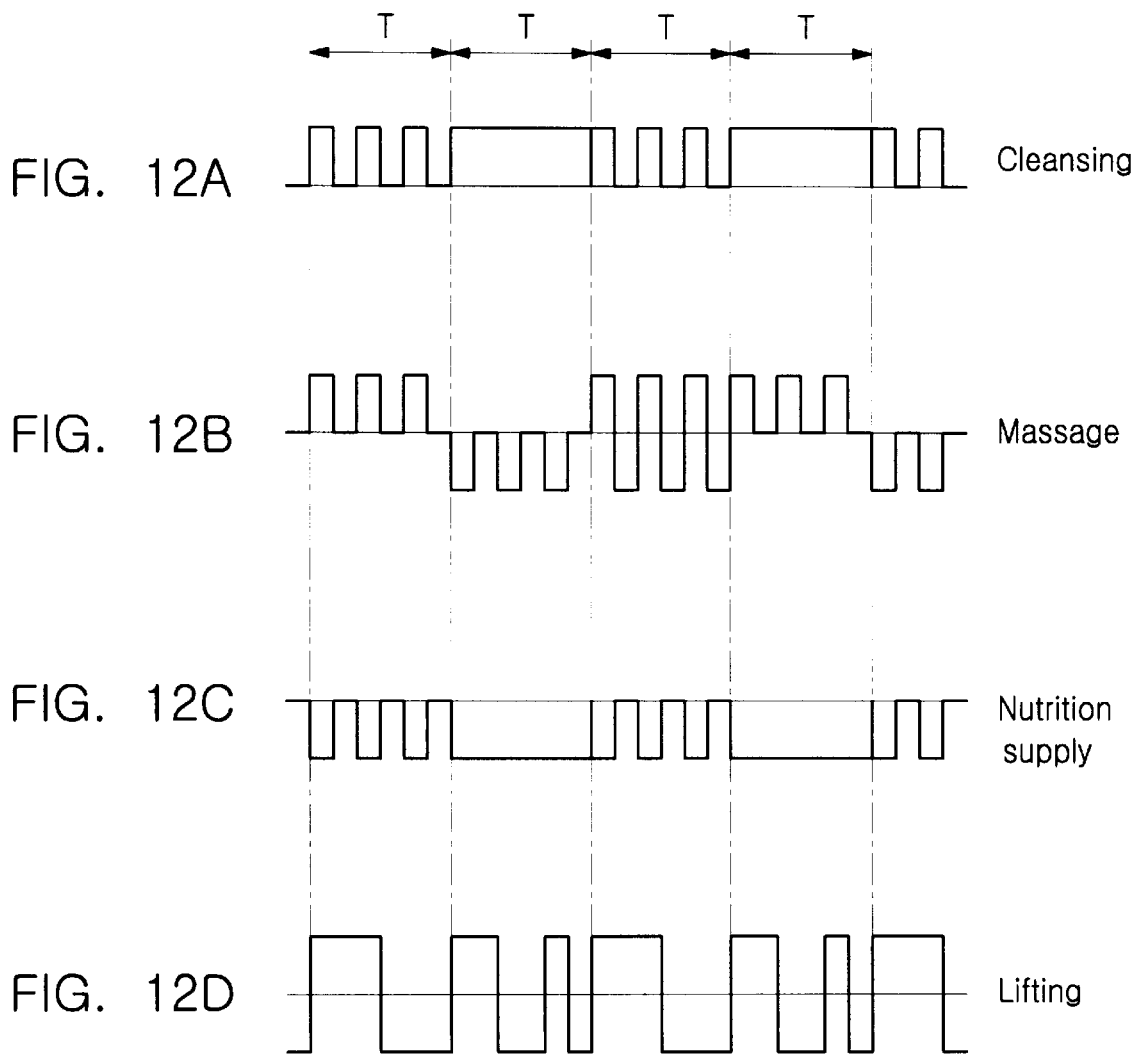

CONTROL DEVICE AND METHOD OF PORTABLE SKIN BEAUTIFYING APPARATUS

BACKGROUND OF THE INVENTION

1. Field of the Invention

The present invention generally relates to device and method for controlling a portable skin beautifying apparatus capable of beautifying the human face skin by galvanic ion current, far infrared ray, and vibration, and measuring the skin state.

2. Description of the Related Art

Generally, cosmetic substances have been used as an implement to maintain the beauty and youth by protecting the human face skin from external environments so as not to lose the resilience.

The thick protein protective layer of the skin is disposed below the corneous layer of the outer skin as a protective layer to protect the skin from external environments. The outer skin layer is separated from the dermal layer by the thick protein protective layer. Therefore, even through a cosmetic substance in which bio-substance is contained and which has a excellent skin protective property, is used, it does not remove the waste product stacked in the dermal layer.

Moreover, since alimentation components contained in the cosmetic substance do not deeply approach the dermal layer, the skin protective effect is not sufficient.

Recently, there has been known a skin beautifying apparatus for beautifying the human skin by galvanic ion current, far-infrared ray, or vibration.

Galvanic ion current maintains the current direction and intensity to be constant. Therefore, despite the time elapses, galvanic ion current is very effective in chemically stimulating the skin, enhancing the skin temperature, and accelerating the blood vessel movement. This galvanic ion current accompanies the generation of magnetic force lines and heat.

Far-infrared rays having a frequency range of 660 UMHZ to 940 UMHZ where adsorption amount into the human body is the highest prevent skin aging and accelerate the blood circulation.

Vibration stimulates neurons of the human body and removes the muscle fatigue. However, since the conventional portable beautifying apparatus utilizes only any one among the three elements of galvanic ion current, far-infrared ray, and vibration, it does not maximize the skin beautifying effect, resulting in low reliability of the product.

In addition, since it generates such a galvanic ion current using the battery's electric power, intensity and frequency of the galvanic ion current are very low, resulting in low skin stimulus and low skin beautifying effect.

Moreover, the conventional beautifying apparatus using the galvanic ion current performs a cleansing step, a massage step, a nutrition supplying step, and a lifting step in the named order. The cleansing step outputs a consecutive positive galvanic ion current, the nutrition supplying step outputs a consecutive negative galvanic ion current, and the massage and the lifting steps repeat to output the consecutive positive galvanic ion current during a first selected time and the consecutive negative galvanic ion current during a second selected time. As a result, the conventional beautifying apparatus has a drawback in that the skin stimulus effect is weak and the beautifying effect is very low.

SUMMARY OF THE INVENTION

Accordingly, it is an object of the present invention to provide a control device and method of a portable beautifying apparatus having an excellent skin beautifying effect by elevating the battery's power and generating galvanic ion current having high frequency.

It is another object of the invention to provide a control device and method of a portable beautifying apparatus capable of periodically varying a flow direction of the galvanic ion current.

It is yet another object of the invention to provide a control device and method of a portable beautifying apparatus capable of beautifying the human face skin by supplying far-infrared ray into the face skin along with the galvanic ion current and selectively providing the face skin with vibration.

It is still yet another object of the invention to provide a control device and method of a portable beautifying apparatus capable of allowing a user to easily measure and check user's own face skin state.

To accomplish these objects and other advantages, according to one aspect of the present invention, there is provided a control method of a portable beautifying apparatus comprising the steps of: a first step performing an initializing operation by turning on an electric power and determining whether or not a key signal is input; a second step setting a skin beautifying step according to the key signal when the key signal is input in the first step and performing skin measurement; a third step performing the skin measurement when the key signal is not input in the first step but the skin measurement is being performed, and determining a present beautifying step when the skin measurement is not being performed and performing the beautifying operation; a fourth step alternatively outputting a discrete positive galvanic ion current having a first frequency and a consecutive positive galvanic ion current for a first time period when the beautifying step determined in the third step is a cleansing step, and simultaneously setting a massage step after outputting far-infrared ray and vibration operations; a fifth step repeatedly outputting a discrete positive galvanic ion current, a discrete negative galvanic ion current, and a positive and negative alternating galvanic current for a second time period each of which has a second frequency when the present beautifying step determined in the third step is the massage step, and setting a nutrition supply step after outputting a far-infrared ray and vibration operations; a sixth step repeatedly outputting a discrete negative galvanic ion current having a third frequency and a consecutive negative galvanic ion current for a third time period when the present beautifying step determined in the third step is the nutrition supply step, and setting a lifting step after outputting far-infrared ray and vibration operations; and a seventh step repeatedly outputting a positive and negative alternating galvanic ion current varied for a selected time within a set frequency range when the present beautifying step determined in the sixth step is the lifting step, and ending the skin beautifying steps after outputting far-infrared ray and vibration operations.

According to another aspect of the present invention, there is provided a control device of a portable beautifying apparatus including: a microcomputer for controlling the whole operation of the beautifying apparatus; a key input part for inputting into the microcomputer an operation command selected by user; a galvanic ion current output part for elevating a battery's power to a level and outputting galvanic ion current according to the control of the microcomputer; a galvanic ion current detecting part for determining whether or not the galvanic ion current output from the galvanic ion current output part flows onto the user's face skin; a vibration generating part for generating a vibration according to the control of the microcomputer; and a far-infrared ray generating part for generating a far-infrared ray according to the control of the microcomputer.

BRIEF DESCRIPTION OF THE DRAWINGS

The above objects and other advantages of the present invention will become more apparent by describing in detail a preferred embodiment thereof with reference to the attached drawings in which:

FIG. 12a to FIG. 12d are waveform diagrams showing waveforms of galvanic ion currents according the beautifying steps.

DETAILED DESCRIPTION OF THE INVENTION

Hereinafter, a control device and method of a portable beautifying apparatus are described with reference to the accompanying drawings.

Figure 1:
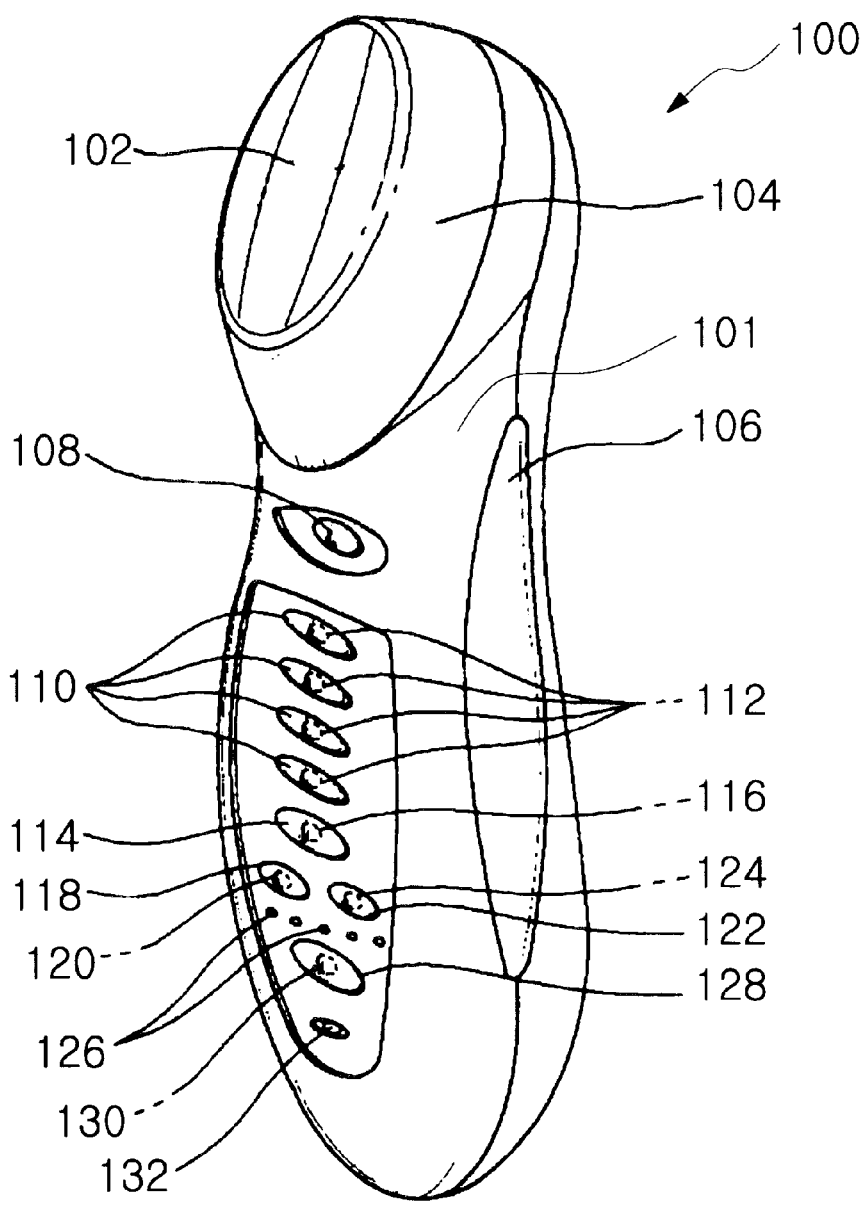
FIG. 1 is a perspective view showing the appearance of a portable beautifying apparatus according the present invention.

FIG. 1 is a perspective view showing the appearance of a portable beautifying apparatus 100 according one embodiment of the present invention.

Reference numeral 101 is the main body of the portable beautifying apparatus. A face skin contact part 102 is disposed at the upper front of the main body 100. The face skin contact part 102 is coupled to a far-infrared output part 104 in which multiple far-infrared ray lamps UD1, UD2, and UD3 for outputting far-infrared rays are equipped at the inside of the far-infrared output part 104. At both sides of left and right sides of the main body 100, there is disposed a pair of grounding parts 106 contacting with the palm of the hand while using the apparatus 100.

Reference Numeral 108 represents a power key turning on or off the apparatus. Below the power key 108, multiple display windows 110 are disposed, each of which displays the present beautifying operation, i.e., cleansing step, massage step, nutrition supply step, or lifting step of the beautifying apparatus. Inside the display window 110, there are disposed multiple light emitting diodes 112 in order to respectively display the cleansing step, the massage step, the nutrition supply step, and the lifting step.

Also, below the display windows 110, an operation selection key 114 is disposed, which selects the present operation to any one of the cleansing step, the massage step, the nutrition supply step, and the lifting step by pressing the key 114 consecutively. The operation selection key 114 is provided with an LED 116 therein.

In order to select any one operation mode of galvanic ion current, far-infrared ray, and vibration operations and control the intensity of the selected operation mode as "strong" or "weak", a pair of mode intensity control keys 118 and 122 are disposed below the operation selection key 114. The weak intensity key 118 is used to select any one operation mode of the three operation modes and control the intensity of the selected mode as weak intensity while the strong intensity key 122 is used to select any one operation mode of the three operation modes and control the intensity of the selected mode as strong intensity. Each of the weak and strong intensity keys 118 and 122 has respective corresponding LEDs 120 and 124 therein.

Below the pair of intensity control keys 118 and 122, there are disposed multiple LEDs 126 representing the skin state as measured. Continuously, below the multiple LEDs 126, there is disposed a skin measuring key 126 commanding the measurement of the skin state. The skin measuring key 126 is also provided with an LED 130 displaying the turn-on state of the skin measuring key 126.

Below the skin measuring key 126, there is disposed an LED 132 displaying a charged state of the battery equipped in the body 100.

Figure 2:
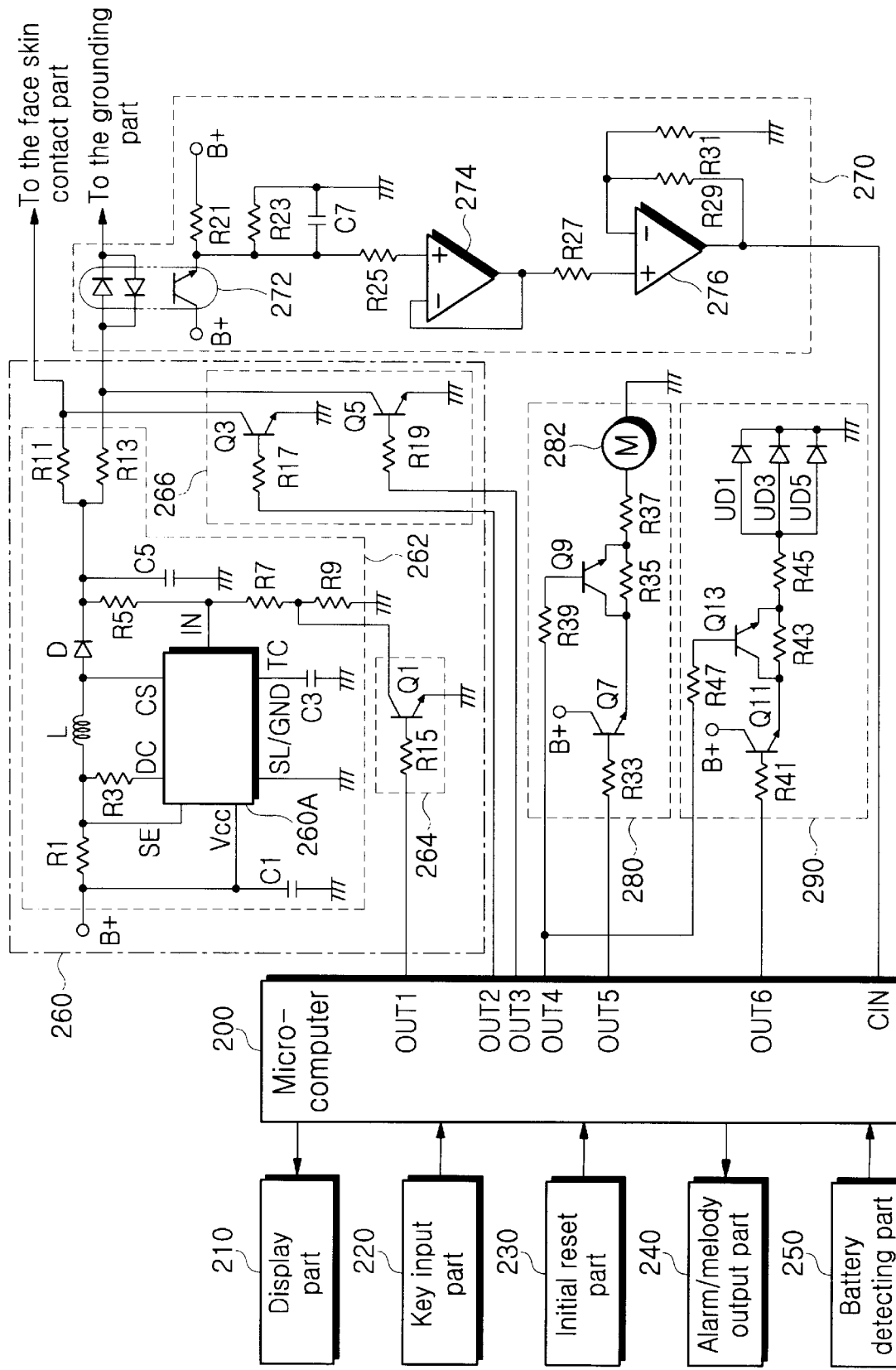
FIG. 2 is a circuit diagram showing a control device used in the apparatus of FIG. 1.

FIG. 2 is a circuit diagram of a control device adapted for the beautifying apparatus of FIG. 1.

Here, reference numeral 200 represents a microcomputer for controlling the whole operation of the beautifying apparatus, and reference numeral 210 represents a display part for displaying the present operation by selectively turning on or off the LEDs 112, 116, 120, 124, 126, 130, and 132 according to the control of the microcomputer 200.

Reference numeral 220 represents a key input part for inputting an operation command generated by pushing the power key 108, the operation selection key 114, the weak intensity key 118, and the strong intensity key 122 into the microcomputer 200.

Reference numeral 230 represents a reset key for resetting the microcomputer 200 for a selected time at an initial time on which electric power B+ is supplied. Reference numeral 240 represents an alarm/melody generating part for generating an alarm or a melody according to the control of the microcomputer 200. Reference numeral 250 represents a battery detecting part for detecting the charged amount of carriers stored in the battery and inputting the detected battery status into the microcomputer 200.

Reference numeral 260 represents a galvanic ion current output part for outputting galvanic ion current according to the control of the microcomputer 200.

The galvanic ion current output part 260 includes a DC/DC converting part 262 for enhancing the battery's power to a selected level, a power level control part for controlling the output power level of the DC/DC converting part 262, and a galvanic ion current polarity switching part 266 for switching the polarity of the galvanic ion current output to the face skin contact part 102 from the DC/DC converting part 262.

The DC/DC converting part 262 includes a DC-DC converting chip 260A having a serial number NJM2360, and fabricated and sold by New Japan Radio Co., Ltd.

A switching limit/ground terminal SL/GND of the DC-DC converting chip 260A is grounded and a timing capacitor terminal TC is connected to a condenser C3. The power B+ is connected to a ground condenser C1 and a ground terminal Vcc of the DC-DC converting chip 260A. The power B+ is also connected to a sensing terminal SE of the chip 260A through a resistor R1, to an output driving terminal DC through the resistor R1 and a resistor R3, to a switching collector terminal CS through the resistor R1 an inductor L, and to a ground condenser C5 through the resistor R1, an inductor L, and a diode D. Between the diode D and the ground condenser C5, resistors R5, R7, and R9 are connected in serial. The connecting point between the resistors R5 and R7 is connected to a comparing voltage inversion input terminal IN. The output voltage flowing through the diode D is respectively applied to the face skin contact part 102 through a resistor R11 and to the grounding part 106 through a resistor R13. Here, the resistors R11 and R13 are connected in parallel.

The power level control part 264 includes a transistor Q1 comprising emitter, base, and collector and a resistor R15 connected to the base of the transistor Q1. The base of the transistor Q1 is connected to the output terminal OUT1 of the microcomputer 200 through the resistor R15, the collector of the transistor Q1 is connected between the resistors R7 and R9 of the galvanic ion current output part 260. As the transistor Q1 turns on or off, an input voltage of the comparing voltage inversion input terminal IN of the DC-DC converting chip 260A varies and whereby an output voltage of the switching collector terminal CS of the chip 260A.

The galvanic ion current polarity switching part 266 includes transistors Q3 and Q5 whose bases are respectively connected to the output terminals OUT2 and OUT3 through respective resistors R17 and R19. Collector of the transistor Q3 is connected between the resistor R11 and the face skin contact part 102 and collector of the transistor Q5 is connected between the resistor R13 and the grounding part 106. As the transistors Q3 and Q5 selectively turn on or off, positive or negative galvanic ion current is selectively output to the face skin contact part 102.

Reference numeral 270 represents a galvanic ion current detecting part which detects whether or not galvanic ion current flows into the user's face skin through the face skin contact part 102 and the grounding part 106.

The galvanic ion current detecting part 270 includes a photo-coupler 272 connected between the resistor R13 and the grounding part 106. The photo-coupler 272 comprises a light receiving transistor and a pair of LEDs arranged in parallel with a polarity direction different from each other. The light receiving transistor includes a collector which is directly connected to the electric power B+ and an emitter which is connected to the electric power B+ through a resistor R21.

The galvanic ion current detecting part 270 further includes first and second amplifiers 274 and 276. An output of the emitter of the light receiving part is input into the first arithmetic amplifier 274 acting as a buffer through a ground resistor 23, a ground capacitor C7, and a resistor 25. An output of the first amplifier 274 is input into the positive terminal of the second amplifier 276 through a resistor R27. The negative terminal of the second amplifier 276 is connected to the output terminal of the second amplifier 276 through a resistor R29 and is grounded through a resistor R31. The output terminal of the second amplifier 276 is connected to the input terminal CIN of the microcomputer 200.

Reference numeral 280 represents a vibration generating part for generating a vibration according to the control of the microcomputer 200.

The vibration generating part 280 includes first and second transistors Q7 and Q8, and a motor 282. The base of the first transistor Q7 is connected to the output terminal OUT5 of the microcomputer 200 through a resistor R33, the collector thereof is connected to electric power B+, and the emitter thereof is connected to the motor 282 through resistors R35 and R37. The base of the second transistor Q9 is connected to the output terminal OUT4 of the microcomputer 200 through a resistor R39, the collector thereof is connected between the emitter of the first transistor Q7 and the resistor R35, and the emitter thereof is connected between the resistors R35 and R37.

Reference numeral 290 represents a far-infrared ray generating part for generating a far-infrared ray according to the control of the microcomputer 200.

The far-infrared ray generating part 290 includes first and second transistors Q11 and Q13. Base of the first transistor Q11 is connected to the output terminal OUT6 of the microcomputer 200 through a resistor R41, the collector thereof is connected to the electric power B+, and the emitter of thereof is respectively connected to multiple far-infrared diode UD1, UD2, and UD3 through consecutive resistors R43 and R45. The base of the second transistor Q13 is connected to the output terminal OUT4 of the microcomputer 200 through a resistor R47, the collector thereof is connected between the emitter of the first transistor Q11 and the resistor R43, and the emitter of thereof is connected between the resistors R43 and R45.

The control device having the above described construction and arrangement initializes the microcomputer 200 by the initial reset part 230 resetting the microcomputer 200 when the power key 108 of the key input part 220 is pushed to turn on the power and whereby the electric power is supplied.

After the microcomputer 200 is reset, as the user pushes the operation selection key 114, the microcomputer 200 sets a beautifying process which is performed in the order of the cleansing step, massage step, nutrition supply step, lifting step, and cleansing step.

Thereafter, when the user pushes the weak intensity key 118, the microcomputer 200 sets the outputs of the galvanic ion current, far-infrared ray, and vibration to the weak state and simultaneously displays the weak state operation by turning on the corresponding LED 118. Depending on to the pushing time of the weak intensity key 118, the output of the vibration can be controlled from the stop operation to the strong vibration operation.

When the user pushes the strong intensity key 122, the microcomputer 200 sets the outputs of the galvanic ion current, far-infrared ray, and vibration to the strong state and simultaneously displays the strong state operation by turning on the corresponding LED 124. Depending on the pushing time of the strong intensity key 122, the output of the melody can be controlled from the stop operation to the strong operation.

When the user pushes the skin measuring key 128, the microcomputer 200 set the skin measuring operation.

As the battery's power B+ is supplied, the DC-DC converting chip 260A of the galvanic ion current output part 260 operates to output a driving signal to the output driving terminal DC. As the driving signal is output, a high voltage is induced by the inductor L and is output. The high voltage of the inductor L is rectified through the diode D, is smoothed by the capacitor C5 and is converted into a direct current power of galvanic ion current. Thereafter, the converted direct current is output to the user's face skin through the resistors R11 and R13 and the face skin contact part 102, and the grounding part 106.

Here, when the output level of the galvanic ion current is set to the strong level, the microcomputer 200 outputs a low voltage through the output terminal OUT1. The low voltage is applied to the base of the transistor Q1 of the power level control part 264 and turns off the transistor Q1. Accordingly, high voltage is applied to the input terminal IN of the DC-DC converting chip 260A and the galvanic ion current output part 260 outputs high level of galvanic ion current.

Meanwhile, when the output level of the galvanic ion current is set to the weak level, the microcomputer 200 outputs a high voltage through the output terminal OUT1. The high voltage is applied to the base of the transistor Q1 of the power level control part 264 and turns on the transistor Q1. Since the connecting point of the resistors R7 and R9 is equally grounded through the transistor Q1, low voltage is applied to the input terminal IN of the DC-DC converting chip 260A and the galvanic ion current output part 260 outputs low level of galvanic ion current.

The ion current polarity switching part 266 varies the polarity of the ion current output by the galvanic ion current output part 260 according to the control of the microcomputer 200.

In other words, when the microcomputer 200 outputs a low voltage through the output terminal OUT2 and outputs a high voltage through the output terminal OUT3, the transistor Q3 of the ion current polarity switching part 266 turns off and the transistor Q5 turns on. Accordingly, the galvanic ion current output from the galvanic ion current output part 260 flows in the ground through the resistor R11, the face skin contact part 102, the user's face skin, the grounding part 106, the LEDs of the photo-coupler 272, and the transistor Q5 of the galvanic ion current polarity switching part 266 in the named order. Positive galvanic ion current flows in the user's face skin.

When the microcomputer 200 outputs a high voltage through the output terminal OUT2 and outputs a low voltage through the output terminal OUT3, the transistor Q3 of the ion current polarity switching part 266 turns on and the transistor Q5 turns off, unlike the above case. Accordingly, the galvanic ion current output from the galvanic ion current output part 260 flows in the ground through the resistor R13, the LEDs of the photo-coupler 272, the grounding part 106, the user's face skin, the face skin contact part 102, and the transistor Q3 of the galvanic ion current polarity switching part 266 in the named order. Negative galvanic ion current flows in the user's face skin.

When the microcomputer 200 outputs high voltage through the output terminals OUT2 and OUT3, the transistors Q3 and Q5 turn on and accordingly the galvanic ion current does not flow in the user's face skin.

As the galvanic ion current is supplied into the user's face skin, the LEDs of the photo-coupler 272 of the galvanic ion current detecting part 270 emit light. When the light receiving transistor of the photo-coupler 272 receives the light emitted from the LEDs of the photo-coupler 272, it turns on. Accordingly, a predetermined level of detecting signal according to the galvanic ion current flowing into the user's face skin is output through the emitter of the light receiving transistor. The detecting signal is amplified through the first buffer 272 acting as the resistor and buffer, is secondly amplified through the second buffer 276 including the resistors R27, R28 and R31, and is input into the input terminal CIN of the microcomputer 200. Accordingly, the user can determine whether the galvanic ion current is output into the user's face skin, from the input signal of the input terminal CIN of the microcomputer 200.

When user pushes the skin measuring key 128 in order to select the skin measuring operation, the microcomputer 200 converts an analog detecting signal input from the galvanic ion current detecting part 270 into a digital signal, determines the skin state from the converted digital signal level, selectively turns on or off the LED 126 to display whether the user's skin state is dry, normal, or fat, so that user can determines user's skin state.

When the vibration operation is selected, the microcomputer 200 outputs a high voltage through the output terminal OUT5. The high voltage is applied to the base of the transistor Q7 through the resistor R33 of the vibration generating part 280 to turn on the transistor Q7. Accordingly, the power B+ is applied to the motor 282 through the transistor Q7 and the resistors R35 and R37 in the named order, so that the motor 282 is driven at a comparatively slow speed.

The motor 282 has an eccentric cam (not shown). Therefore, as the motor 282 is driven, the eccentric cam is accordingly rotated and whereby a weak level of vibration is generated.

Meanwhile, when user selects the strong level of the vibration operation, the microcomputer 200 outputs a high voltage through the output terminal OUT4. The high voltage is applied to the base of the transistor 09 through the resistor R39 of the vibration generating part 280 to turn on the transistor Q9. Accordingly, the power B+ having a relatively high voltage is applied to the motor 282 through the transistors Q7 and Q9 and the resistors R37 in the named order, so that the motor 282 is driven at a comparatively rapid speed and whereby a strong level of vibration is generated.

When far-infrared output is selected, the microcomputer 200 outputs a high voltage through the output terminal OUT7. The high voltage is applied to the base of the transistor Q11 through the resistor R41 of the far-infrared ray generating part 290, so that the transistor Q11 is turned on. At this time, the power B+ is respectively applied to the multiple far-infrared ray diodes UD1, UD3, and UD5 through the transistor Q11 and the resistors R43 and R45 in the named order, so that the diodes UD1, UD3, and UD5 are turned on and a weak level of far-infrared ray is output to the user's face skin through the far-infrared output part 104.

Here, when the user selects the strong level, the microcomputer 200 outputs a high voltage through the output terminal OUT4. The high voltage is applied to the base of the transistor Q13 through the resistor 47, so that the transistor Q13 is turned on. At this time, the power B+ is respectively applied to the multiple far-infrared ray diodes UD1, UD3, and UD5 through the transistors Q11 and Q13, and the resistor R45, so that a large amount of current flows through the diodes UD1, UD3, and UD5 and whereby a high level of far-infrared ray is output.

FIG. 3 to FIG. 11 are flow charts showing a control method according to one embodiment of the present invention.

Figure 3:
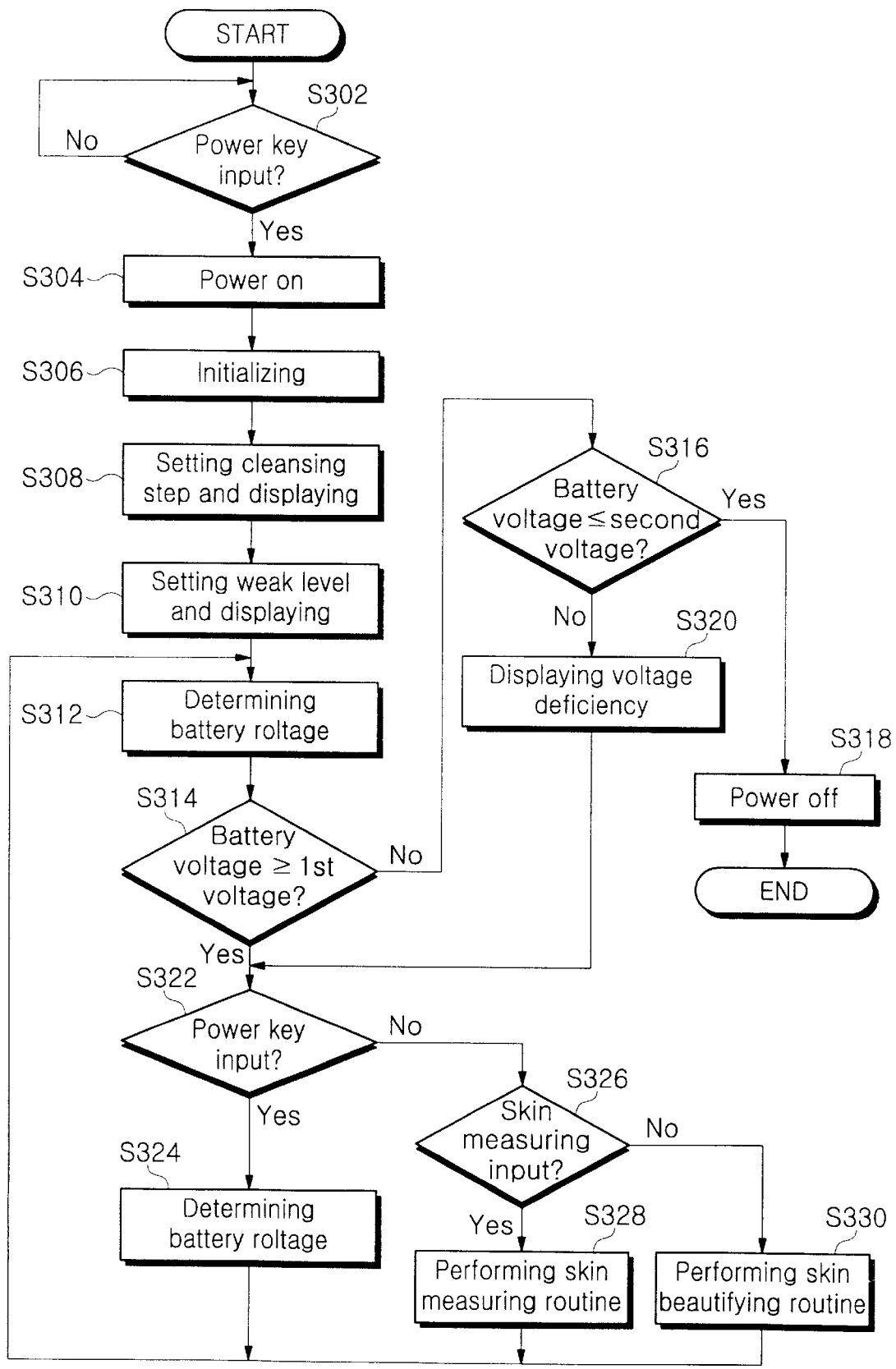
FIG. 3 is a flow chart showing a main routine for controlling the apparatus of FIG. 1.

Referring to FIG. 3, the microcomputer 220 determines whether or not the power key of the key input part 220 is input (S302). The microcomputer 200 turns on the power when the power key is input (S304). Thereafter, the microcomputer 200 is initialized according to the output signal of the initial reset part 230 (S306).

After the initializing step (S306) is completed, the microcomputer 200 selects the cleansing step which is the first step of the beautifying process and displays the selected cleansing step by turning on the corresponding LED (S308). Thereafter, the microcomputer 200 designates the outputs of the galvanic ion current, far-infrared ray and vibration operations as the weak level (S310) and then determines the battery's charged state from the output signal of the battery detecting part 250 (S312).

When the battery's charged voltage is less than a first critical voltage (S314), it is again determined whether the battery's charged voltage is less than or equal to a second critical voltage which is less than the first critical voltage (S316). When the battery's charged voltage is less than or equal to the second critical voltage, the microcomputer 200 turns off the power to prevent the battery from being discharged over a selected level (S318).

When the battery's charged voltage is greater than the second critical voltage, the microcomputer 200 determines that the battery's power is not over-discharged, turns on the LED 132 to display the deficiency of the battery's power (S320), and determines whether or not the power key signal is input (S322).

From the power key input determining step (S322), when it is determined that the key signal has been input, a key signal input routine (later described) is performed (S324). When it is determined that the key signal has not been input during the power key signal input step (S322), the microcomputer 200 determines whether the skin measuring step is being performed (S326). When it is determined that the skin measuring step is being performed, a skin measuring routine (later described) is performed (S328) and when it is determined that the skin measuring step is not being performed, a skin beautifying routine (later described) is performed (S330).

Figures 1, 4:
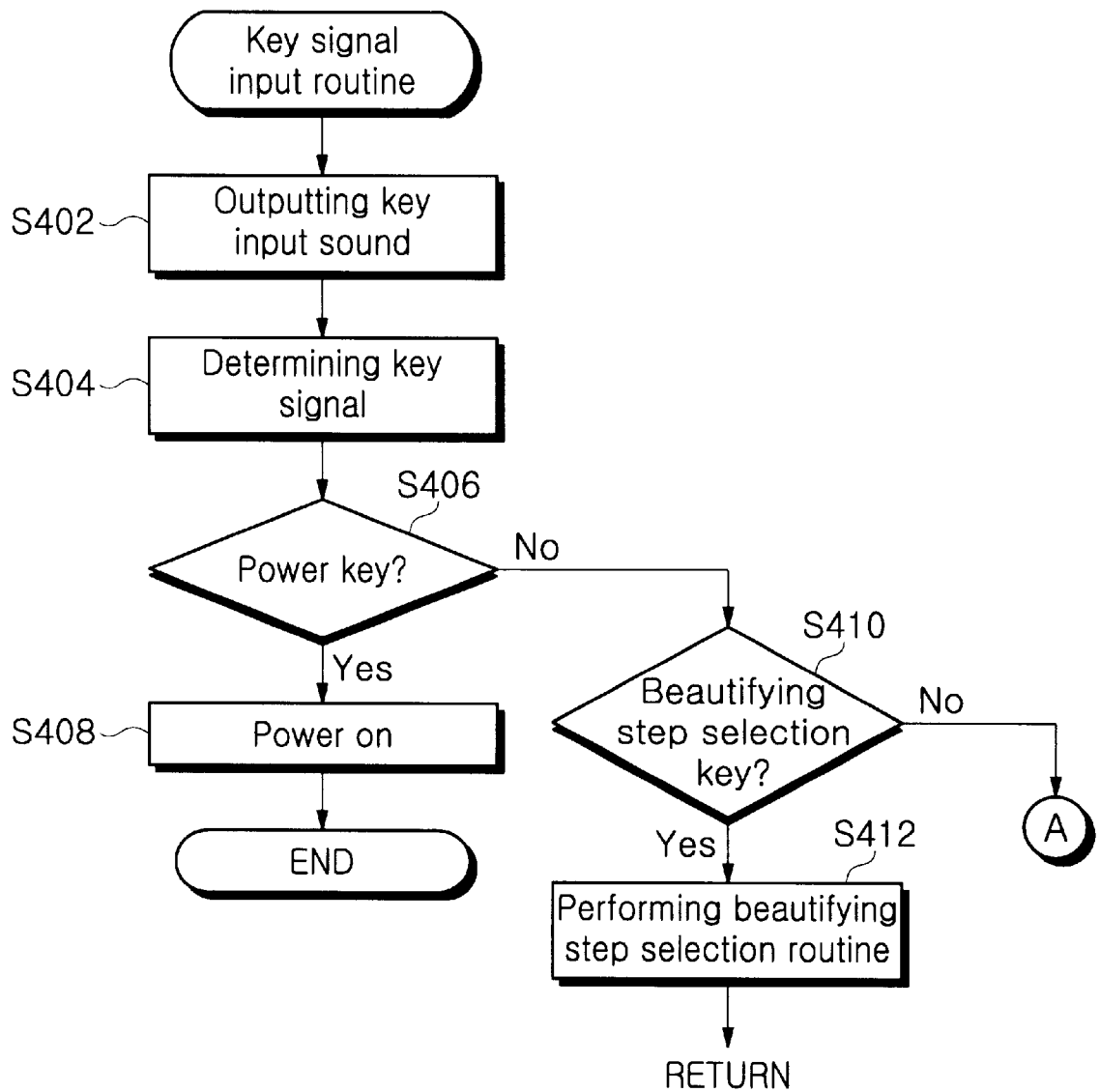
FIG. 4 is a flow chart showing the key signal input routine in the flow chart of FIG. 3.
Figures 2, 4:
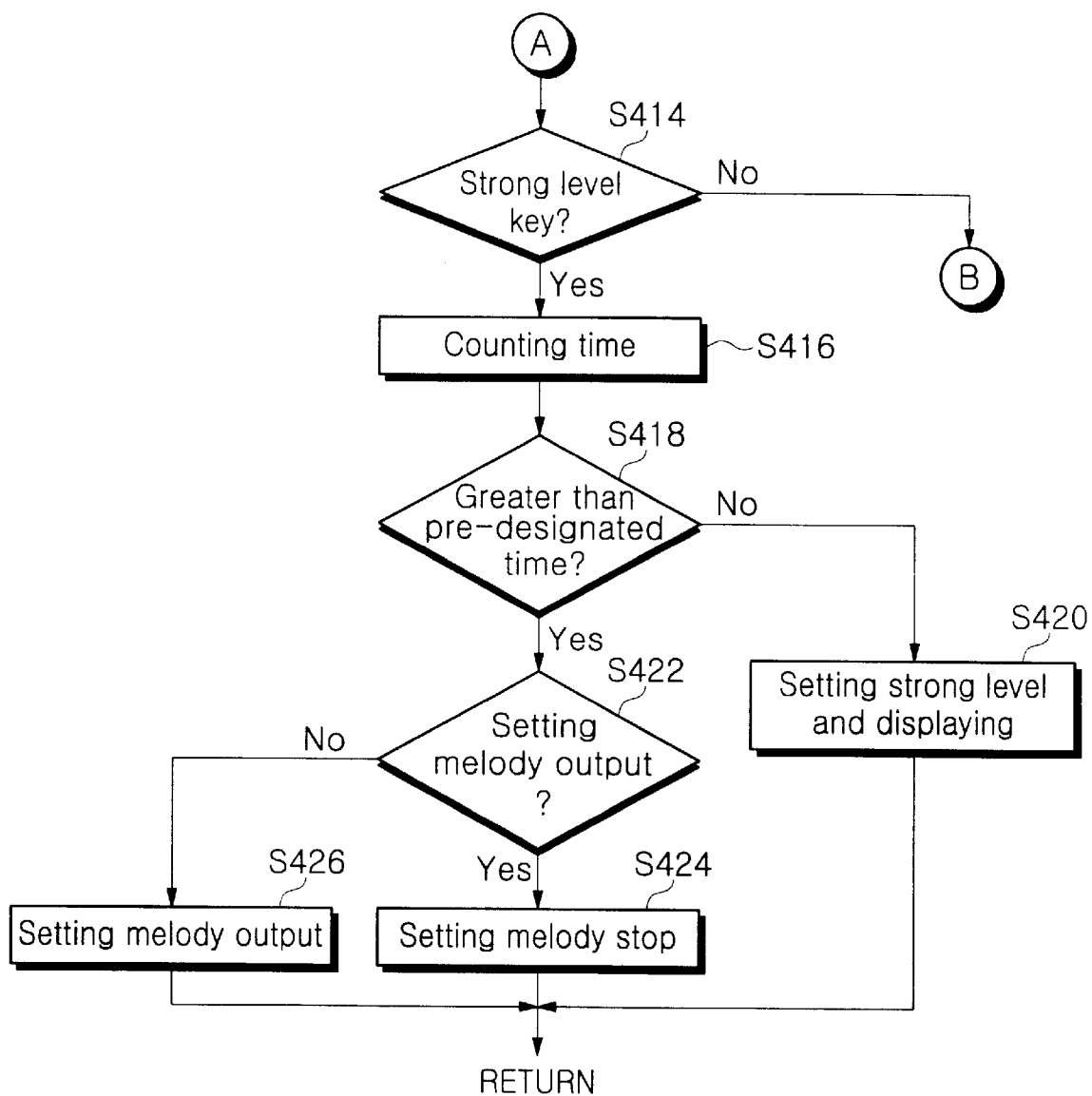
Figure 4:
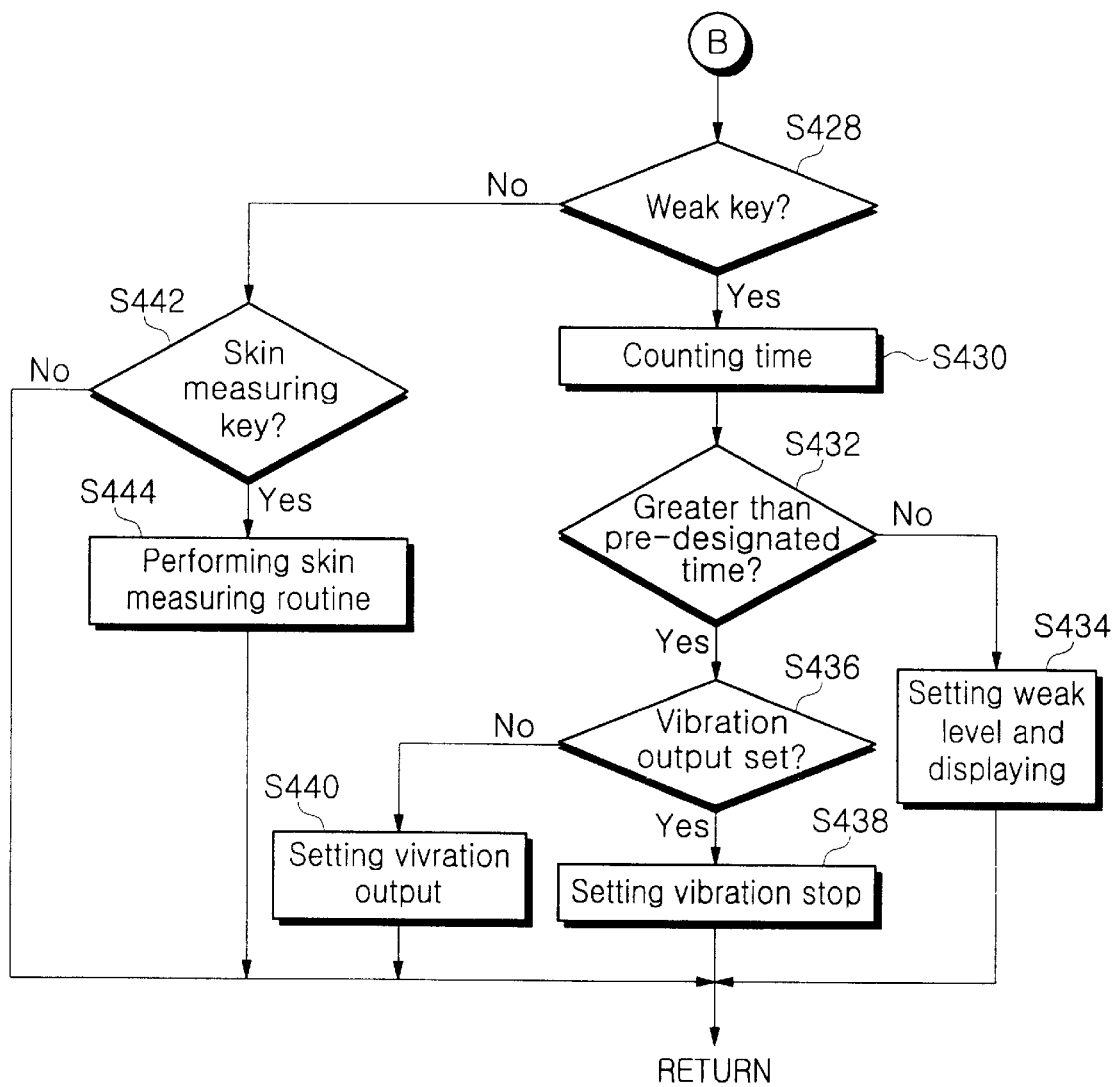
Figure 3:
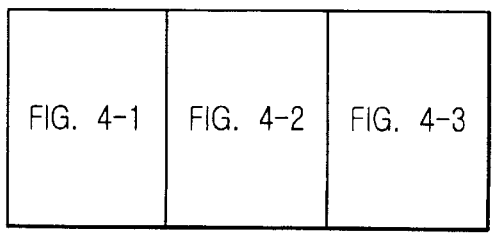

The key signal input routine noted in the key signal input routine performing step S324 is performed as shown in FIG. 4.

The key signal input routine first performs a step of outputting a selected key input sound (S402). The key input sound is output for a selected time by controlling the alarm/melody output part 240 of FIG. 2.

The microcomputer 200 performs a step of determining what the input key signal is (S404).

When it is determined that the input key signal is the power input from the key input determining step (S404), the power is turned off (S408).

When it is determined that the input key signal is not the power input in the key input determining step (S404), the microcomputer 200 determines whether or not the input key signal is the beautifying step selection key input (S410).

When it is determined that the input key signal is the beautifying step selection key input from the beautifying step determining step (S410), a beautifying step selecting routine (later described) is performed.

When it is determined that the key signal is not the beautifying step selection key input from the beautifying step determining step (S410), a step of determining whether or not the input key signal is the strong intensity key input, is performed (S414).

When the key signal is the strong intensity key signal input, an input time of the strong intensity key signal is counted (S418). Thereafter, it is determined that the input time is more than a pre-designated time (S418).

When the input time is less the pre-designated time, output levels of the galvanic ion current, vibration and far-infrared ray are set as the strong level and the strong level setting is displayed.

When the counted time is more than the pre-designated time, it is determined that a melody output is designated (S422).

When a melody output is designated from the melody designation determining step (S422), a command stopping the melody output is designated (S424), while when a melody output is not designated, the melody output is designated (S426).

From the strong intensity key input determining step (S414), when the strong intensity key 122 is not input, it is determined that the weak intensity key 118 is input (S428).

When the weak intensity key is input, an input time of the weak intensity key signal is counted (S430). Thereafter, it is determined that the input time of the weak intensity key signal is more than a pre-designated time (S432).

When the input time is less the pre-designated time, output levels of the galvanic ion current, vibration and far-infrared ray are set as the weak level and the weak level setting is displayed (S434).

Meanwhile, when the input time of the weak intensity key signal is more than the pre-designated time, it is determined whether or not a vibration output command is set (S436).

When the vibration output command is set, a command stopping the vibration is set (S438), while when the vibration output command is not set, the vibration output command is set (S440).

Meanwhile, when it is determined that a skin measuring key signal is input from the step S442 of determining an input of the skin measuring key, a skin measuring routine (to be described later) is performed (S444).

Figure 5:
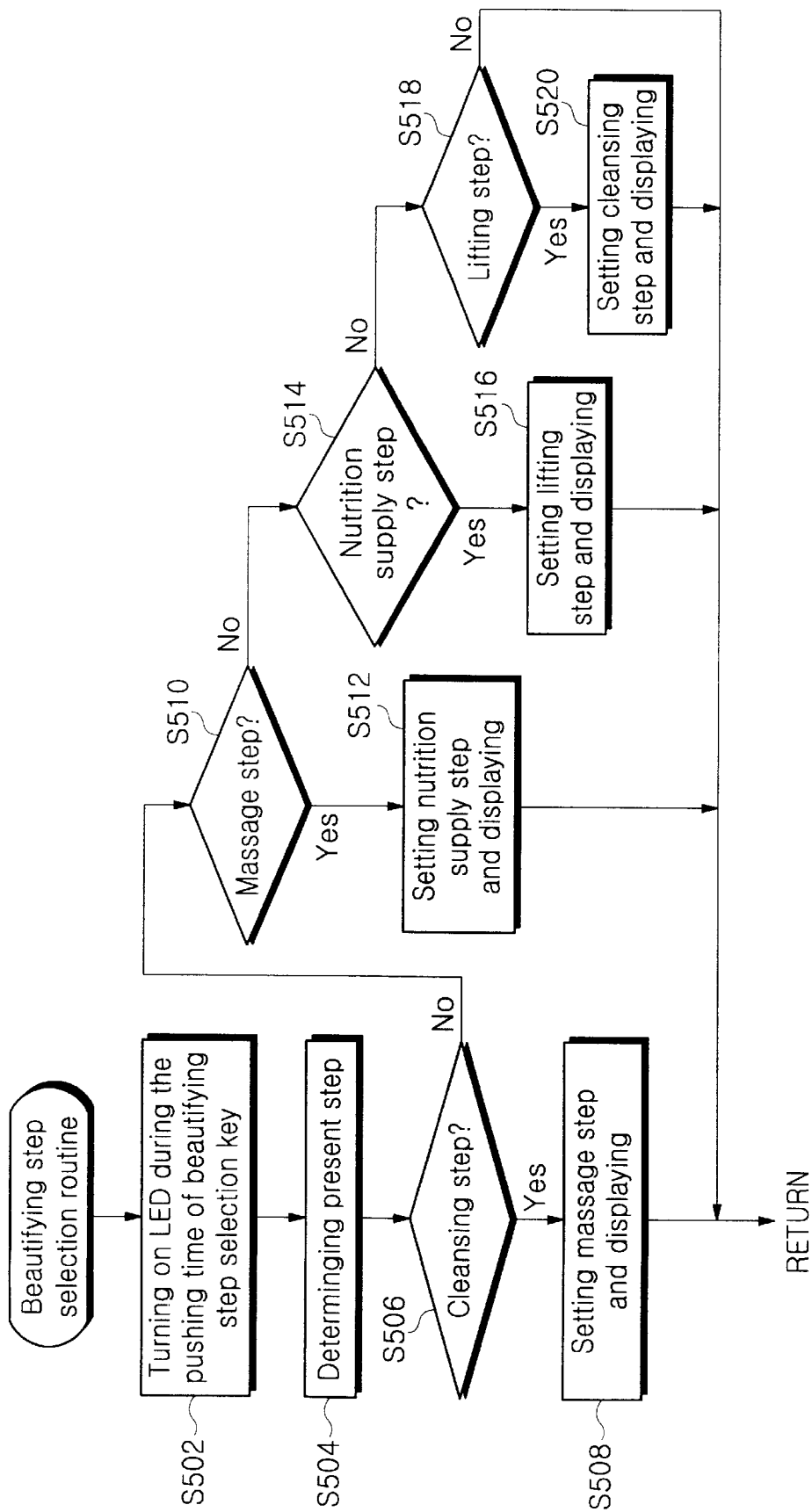
FIG. 5 is a flow chart showing the routine of selecting the beautifying step in FIG. 4.

Referring to FIG. 5, the beautifying step selection routine mentioned in the step S412 of FIG. 4 first performs a step of displaying an input of the beautifying step selection key by turning on the LED 116 during a pushing time of the beautifying step selection key 114. Thereafter, the present beautifying setting step is determined (S504). Afterwards, it is determined whether or not the present set beautifying step is the cleansing step (S506).

When the present set beautifying step is the cleaning step, the massage step is set and is displayed by turning on the corresponding LED 112. While, when the present set beautifying step is not the cleaning step, it is determined whether or not the present set beautifying step is the massage step (S510).

When the present set beautifying step is the massage step, the nutrition supply step is set and is displayed by turning on the corresponding LED 112. While when the present set beautifying step is not the massage step, it is determined whether or not the present set beautifying step is the nutrition supply step (S514).

When the present set beautifying step is the nutrition supply step, the lifting step is performed and is displayed by turning on the corresponding LED 112. While when the present set beautifying step is not the nutrition supply step, it is determined whether or not the present set beautifying step is the lifting step (S518).

When the present set beautifying step is the lifting step, the cleansing step is performed and is displayed by turning on the corresponding LED 112.

In other words, in the beautifying step selection step, as the beautifying step selection key 114 is pushed, the cleansing step, the massage step, the nutrition supply step, the lifting step, and the cleansing step is repeatedly set in the named order.

Figure 6:
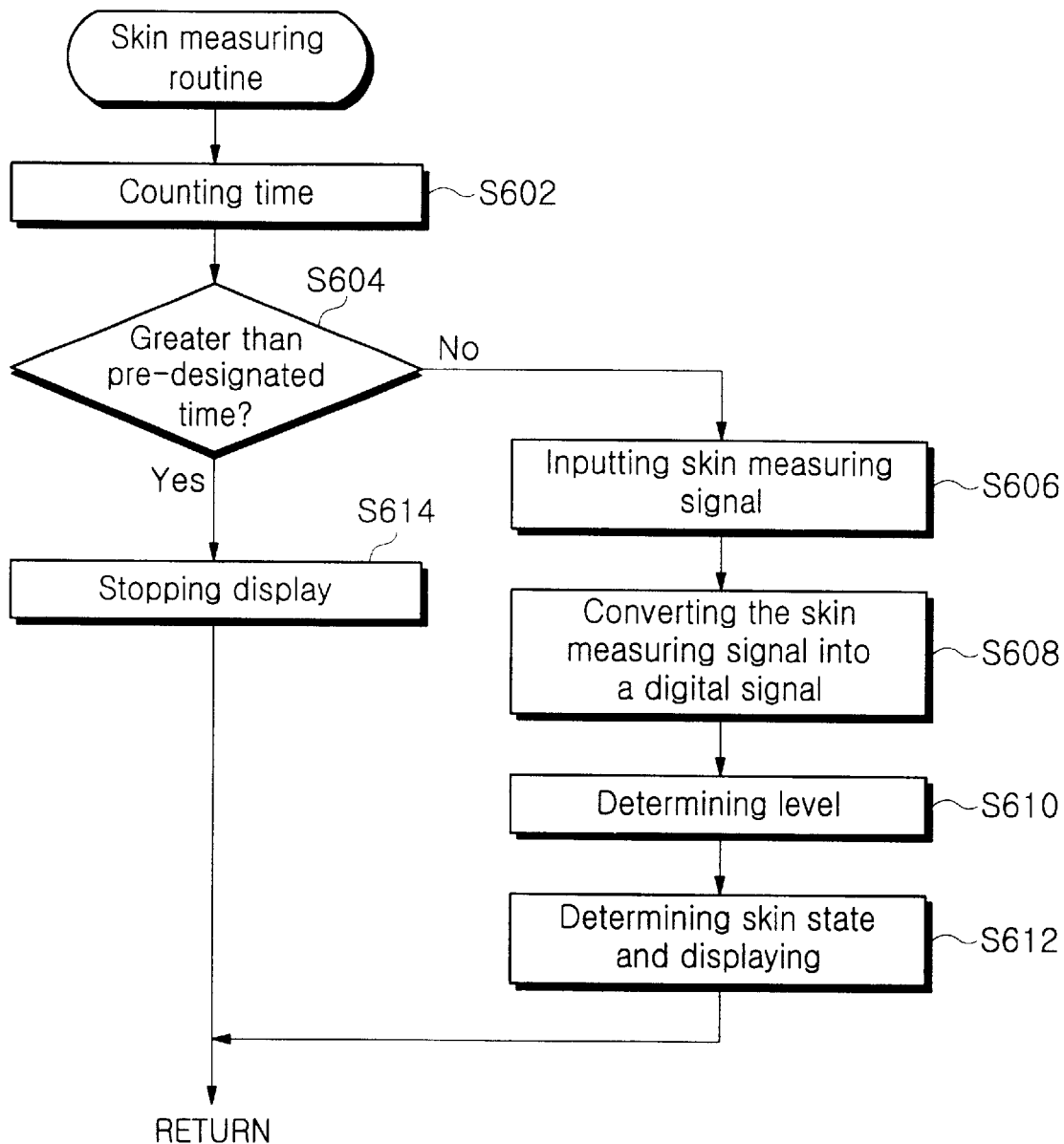
FIG. 6 is a flow chart showing the skin measuring routines of FIGS. 3 and 4.

Referring to FIG. 6, the skin measuring step mentioned in FIG. 3 and FIG. 4 first performs a step of counting the time taken in performing the skin measuring step (S602). Afterwards, it is determined whether or not the counting time is more than a pre-designated time, for example, 20 seconds (S604).

When the counting time is less than the pre-designated time, the skin measuring signal output from the galvanic ion current detecting part 270 is input (S606). Thereafter, the input skin measuring signal is converted into a digital signal (S608). Thereafter, it is determined that the digital signal is at a level (S610). Thereafter, from the determining step (S610) of the level, the skin state is determined and is displayed by selectively turning on the multiple LEDs 126.

For example, when the measured skin state is fat, two LEDs 126 positioned at the left side are turned on, when the measured skin state is normal, LED 126 positioned at the center is turned on, and when the measured skin state is dry, two LEDs 126 positioned at the right side are turned on.

When the counting time is more than the pre-designated time from the pre-designated time determining step (S604), the microcomputer 200 stops to display the skin measuring state and ends the skin measuring operation by turning off all the LEDs 126.

Figure 7:
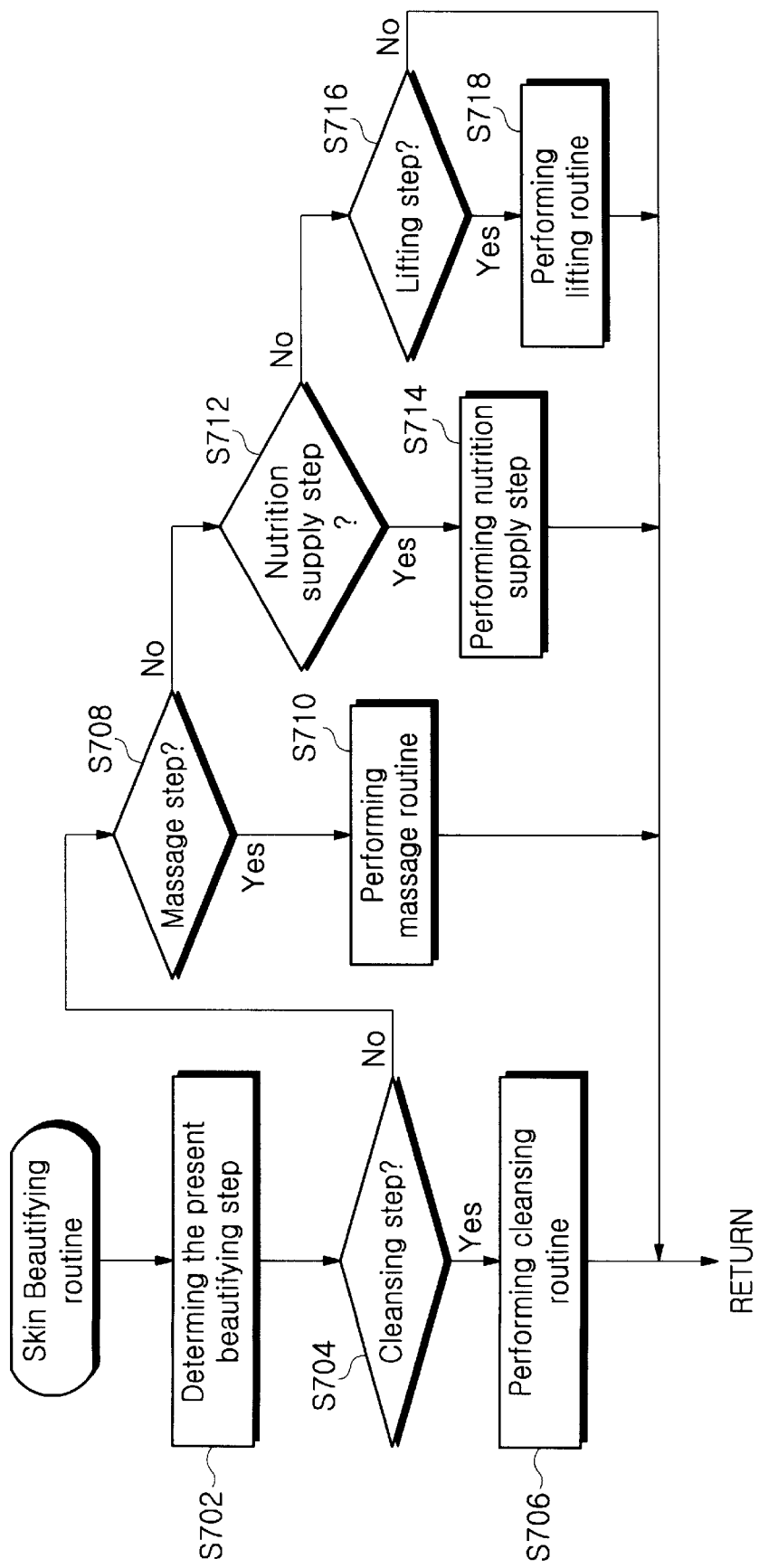
FIG. 7 is a flow chart showing the skin beautifying routine of FIG. 3.

Referring to FIG. 7, the skin beautifying routine mentioned in the step S330 of FIG. 3 first performs a step of determining the present skin beautifying step (S702). Afterwards, it is determined whether or not the present skin beautifying step is the cleansing step.

When the present skin beautifying step is the cleansing step, the cleansing routine is performed (S706) to thereby remove toxins and waste products stacked deeply in the skin.

Meanwhile when the present skin beautifying step is not the cleaning step from the determining step (S704) of the cleansing step, it is determined the present skin beautifying step is the massage step (S708).

When the present skin beautifying step is the massage step, the massage routine (to be described later) is performed (S710) and whereby pores of the face skin is expanded or reduced, resulting in allowing the face skin to be resilient and bright.

Meanwhile when the present skin beautifying step is not the massage step from the determining step (S708) of the massage step, it is determined the present skin beautifying step is the nutrition supply step (S712).

When the present skin beautifying step is the nutrition supply step, the nutrition supply step (to be described later) is performed (S714) and whereby pores of the face skin is expanded or reduced, resulting in allowing the face skin to be resilient and bright.

Figure 8:
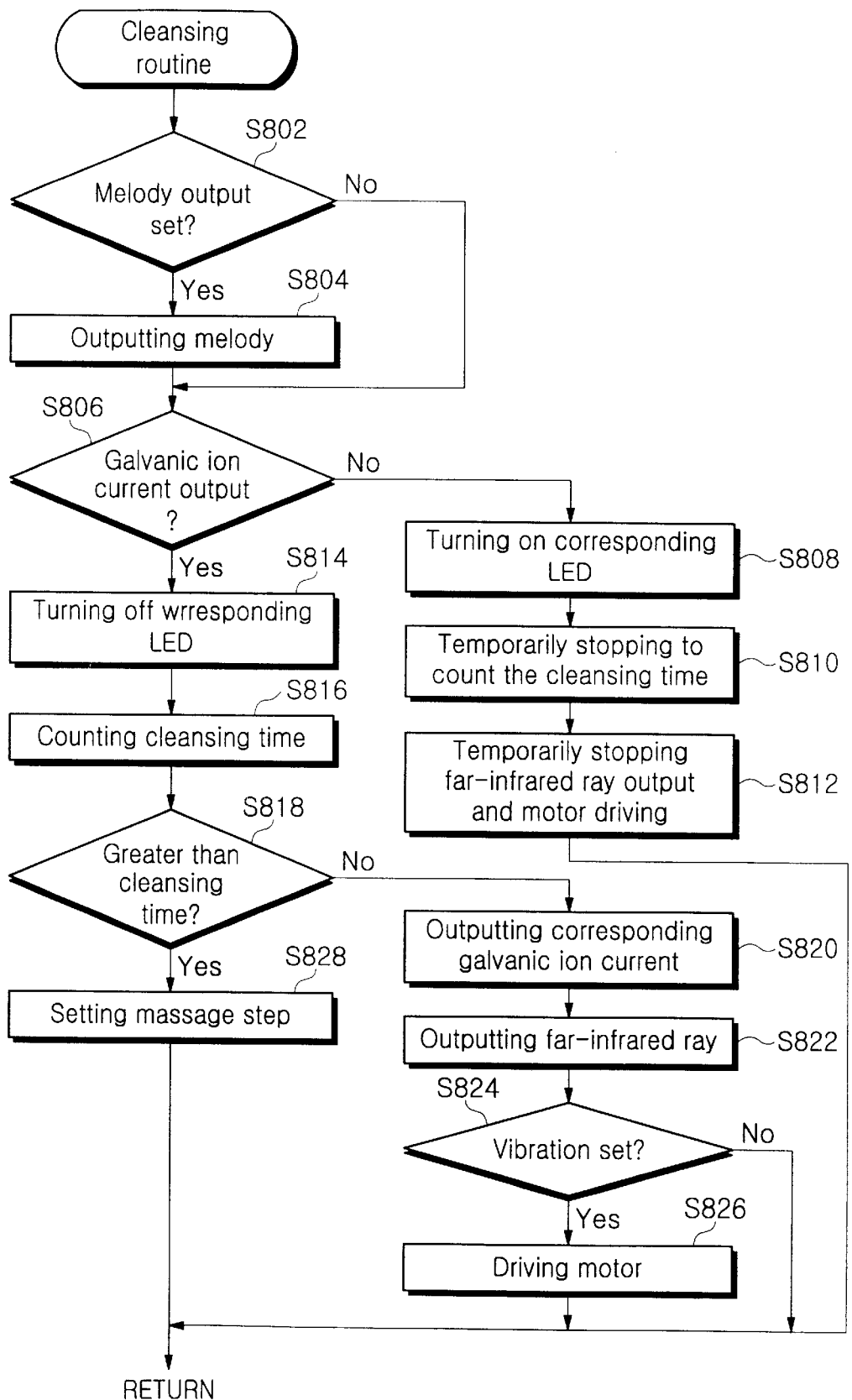
FIG. 8 is a flow chart showing the cleansing routine of FIG. 7.

Referring to FIG. 8, the cleansing routine mentioned in the step S706 of FIG. 7 first determines whether or not the melody output is set (S802). In other words, it is determined whether or not the melody output is set by pushing the strong level key 122 over a pre-designated time.

When the melody output is set from the determining step (S802) of the melody output, the alarm/melody output part 240 outputs a melody by the control of the microcomputer 200 (S804) and the DC-DC converting part 262 of the galvanic ion current output part 260 elevates the power level to a selected level of strong level or weak level according to user's selection. Thereafter, it is determined whether or not the galvanic ion current is output onto the user's face skin from the skin measuring signal output from the galvanic ion current detecting part 270.

When the galvanic ion current is not output onto the user's face skin in the determining step S806, the corresponding LED 112 is turned on and whereby the stop of the cleansing step is displayed and simultaneously it is displayed that the galvanic ion current is not output onto the user's face skin (S808).

Afterwards, it is temporarily stopped to count a time taken in performing the cleansing step (S810) and to output far-infrared ray and operate the motor 282 (S812).

When the galvanic ion current is output onto the user's face skin in the step S806, the microcomputer 200 turns off the corresponding LED 112 and displays performing the cleansing step. In the step S816, the microcomputer 200 counts a time taken in performing the cleansing step and thereafter determines whether or not the counting time is more than the pre-designated time.

In other words, it is determined whether or not the counting time is more than the pre-designated time by counting only the time performing the cleansing step after the galvanic ion current is output onto the user's face skin.

When the counting time of the cleansing step is less than the pre-designated time in the step S818, the microcomputer 200 outputs a galvanic ion current corresponding to the cleansing step in the step S820.

As shown in FIG. 12A, the galvanic ion current corresponding to the cleansing step has one period of 2T and includes a discrete positive galvanic ion current output for a first selected time T, for example 2–3 seconds, and a consecutive positive galvanic ion current output for a second selected time T, for example, 2–3 seconds. The discrete positive galvanic ion current and the consecutive positive galvanic ion current are alternatively output for given time periods. Here, the positive galvanic ion current has a frequency of approximately 2–10 Hz.

Thereafter, a far-infrared ray is output by controlling the far-infrared ray generating part 290 according to user's selection level of strong or weak level (S822). Thereafter, it is determined whether or not the vibration step is set (S824).

That is, it is determined whether or not the vibration step is set by pushing the weak level key 122 in the step S428 of FIG. 4.

When the vibration step has been set, the microcomputer 200 drives the motor 282 to generate the vibration by controlling the vibration generating part 280 according to user's selection of the strong or weak level.

Thus, the cleansing step repeats to output a positive galvanic ion current having a strong or weak level and a selected frequency per a specific period T, outputs the far-infrared ray, and generates the vibration, thereby removing toxins and waste products stacked deeply in the skin.

In this state, when the performing time of the cleansing step which is set in the step S818 elapses, the microcomputer 200 sets the following skin beautifying step of the massage step and ends the cleansing step (S828).

Figure 9:
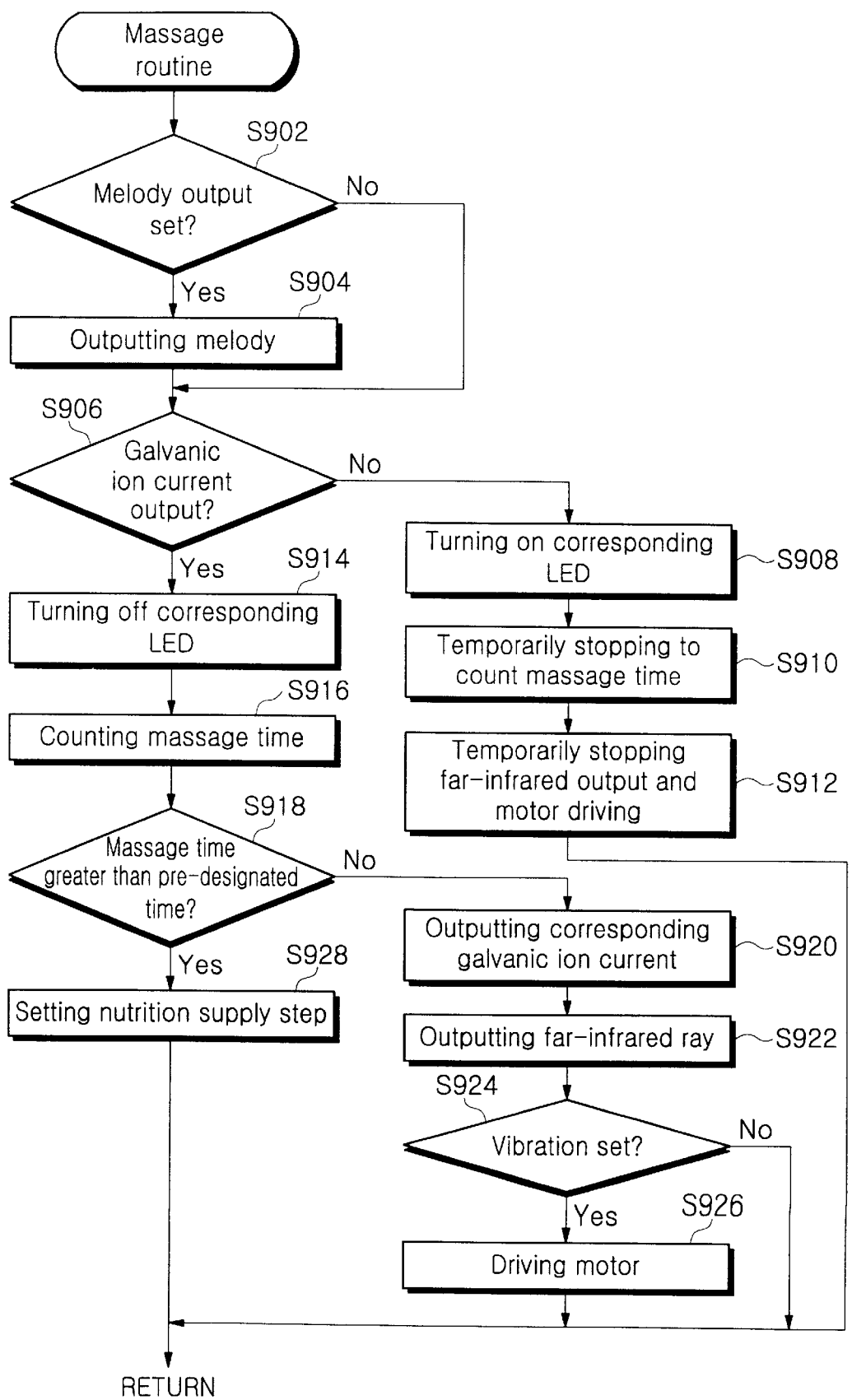
FIG. 9 is a flow chart showing the massage routine of FIG. 7.

Referring to FIG. 9, the massage routine mentioned in the step S710 of FIG. 7 first determines whether or not the melody output is set (S902).

When the melody output is set from the determining step (S902) of the melody output, the alarm/melody output part 240 outputs a melody by the control of the microcomputer 200 (S904) and the DC-DC converting part 262 of the galvanic ion current output part 260 elevates the power level to a selected level of strong level or weak level according to user's selection.

Thereafter, it is determined whether or not the galvanic ion current is output onto the user's face skin from the skin measuring signal output from the galvanic ion current detecting part 270.

When the galvanic ion current is not output onto the user's face skin in the determining step S906, the corresponding LED 112 is turned on and whereby the stop of the massage step is displayed and simultaneously it is displayed that the galvanic ion current is not output onto the user's face skin (S908).

Afterwards, it is temporarily stopped to count a time performing the massage step (S910) and simultaneously stopped to output far-infrared ray and operate the motor 282 (S912).

When the galvanic ion current is output onto the user's face skin in the step S906, the microcomputer 200 turns off the corresponding LED 112 and displays performing the massage step. In the step S916, the microcomputer 200 counts a time taken in performing the massage step and in the step S918 thereafter determines whether or not the counting time is more than the pre-designated time.

When the counting time of the massage step is less than the pre-designated time in the step S918, the microcomputer 200 outputs a galvanic ion current corresponding to the massage step in the step S920.

As shown in FIG. 12B, the galvanic ion current corresponding to the massage step has one period of 3T and includes a discrete positive galvanic ion current output for a first time period of T, for example, 2–3 seconds, a discrete negative galvanic ion current output for a second time period of T, for example, 2–3 seconds, and a positive and negative alternating ion current output for a third time period of T, for example, 2–3 seconds. The positive galvanic ion current, the negative galvanic ion current, and the positive and negative alternating galvanic ion current are repeatedly output in the named order for given time periods and each of them has a frequency of 2–10 Hz.

Thereafter, a far-infrared ray is output by controlling the far-infrared ray generating part 290 according to user's selection level of strong or weak level (S922). Thereafter, it is determined whether or not the vibration step is set (S924).

When the vibration step has been set, the microcomputer 200 drives the motor 282 to generate a vibration by controlling the vibration generating part 280 according to user's selection of the strong or weak level.

Thus, the massage step repeats to output a positive galvanic ion current and a negative galvanic ion current each having a strong or weak level and a selected frequency per a specific period T, outputs the far-infrared ray, and generates the vibration, thereby removing toxins and waste products stacked deeply in the skin, whereby pores of the face skin is expanded or reduced, resulting in allowing the face skin to be resilient and bright.

In this state, when the performing time of the massage step which is set in the step S918 elapses, the microcomputer 200 sets the following skin beautifying step of the nutrition supply step and ends the massage step (S928).

Figure 10:
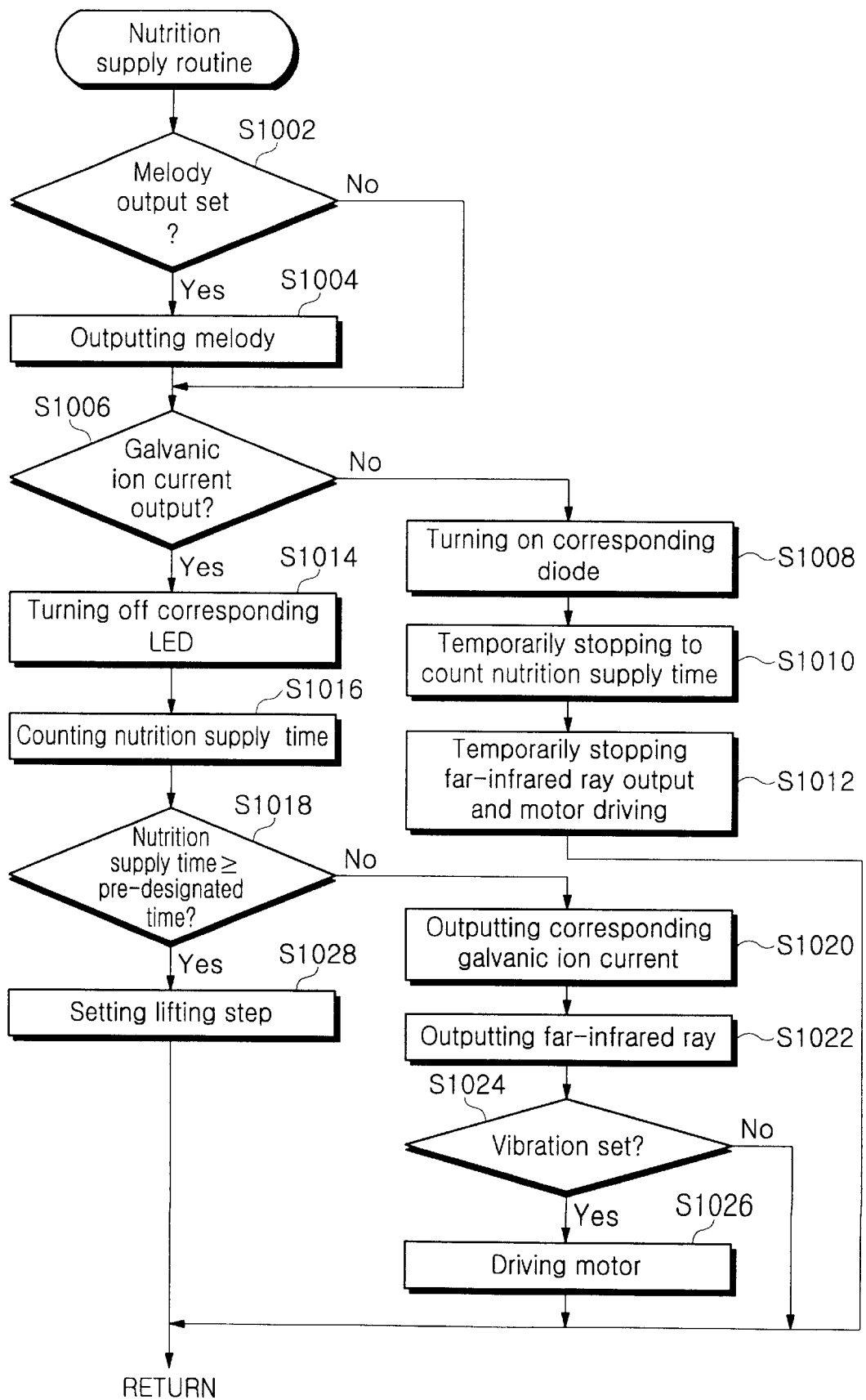
FIG. 10 is a flow chart showing the nutrition supplying routine of FIG. 7.

Referring to FIG. 10, the nutrition supply routine mentioned in the step S714 of FIG. 7 first determines whether or not the melody output has been set (S1002).

When the melody output has been set from the determining step (S1002) of the melody output, the alarm/melody output part 240 outputs a melody by the control of the microcomputer 200 (S1004). Thereafter, it is determined whether or not the galvanic ion current is output onto the user's face skin (S1006).

When the galvanic ion current is not output onto the user's face skin in the galvanic ion current output determining step S1006, the corresponding LED 112 is turned on (S1008) and whereby it is displayed that the nutrition supply step is stopped and simultaneously it is displayed that the galvanic ion current is not output onto the user's face skin.

Afterwards, it is temporarily stopped to count a time taken in performing the nutrition supply step in the step S1010 and to output far-infrared ray and operate the motor 282 in the step S1012.

When the galvanic ion current is output onto the user's face skin in the step S1006, the microcomputer 200 turns off the corresponding LED 112 in the step S1014, thereby displaying performing the nutrition supply step. In the step S1016, the microcomputer 200 counts a time taken in performing the nutrition supply step and thereafter determines whether or not the counting time is greater than the pre-designated time in the step S1018.

When it is determined that the counting time is less than the pre-designated time in the step S1018, the microcomputer outputs a galvanic ion current corresponding to the nutrition supply step in the step S1020.

As shown in FIG. 12C, the galvanic ion current corresponding to the nutrition supply step has one period of 2T and includes a discrete negative galvanic ion current output for a first selected time T and a consecutive negative galvanic ion current output for a second selected time T. The discrete negative galvanic ion current and the consecutive negative galvanic ion current are alternatively output for given time periods. Here, the discrete negative galvanic ion current has a frequency of approximately 2–10 Hz.

Thereafter, a far-infrared ray is output by controlling the far-infrared ray generating part 290 according to user's selection level of strong or weak level (S1022). Thereafter, it is determined whether or not the vibration step has been set (S1024).

When the vibration step has been set, the microcomputer 200 drives the motor 282 to generate the vibration by controlling the vibration generating part 280 according to user's selection of the strong or weak level (S1024).

Thus, the nutrition supply step repeats to output a negative galvanic ion current having a strong or weak level and a selected frequency per a specific period T, outputs the far-infrared ray, and generates the vibration, thereby supplying nutrition to a deep skin.

In this state, when the performing time of the nutrition supply step which is set in the step S1018 elapses, the microcomputer 200 sets the following skin beautifying step of the lifting step and ends the nutrition supply step.

Figure 11:
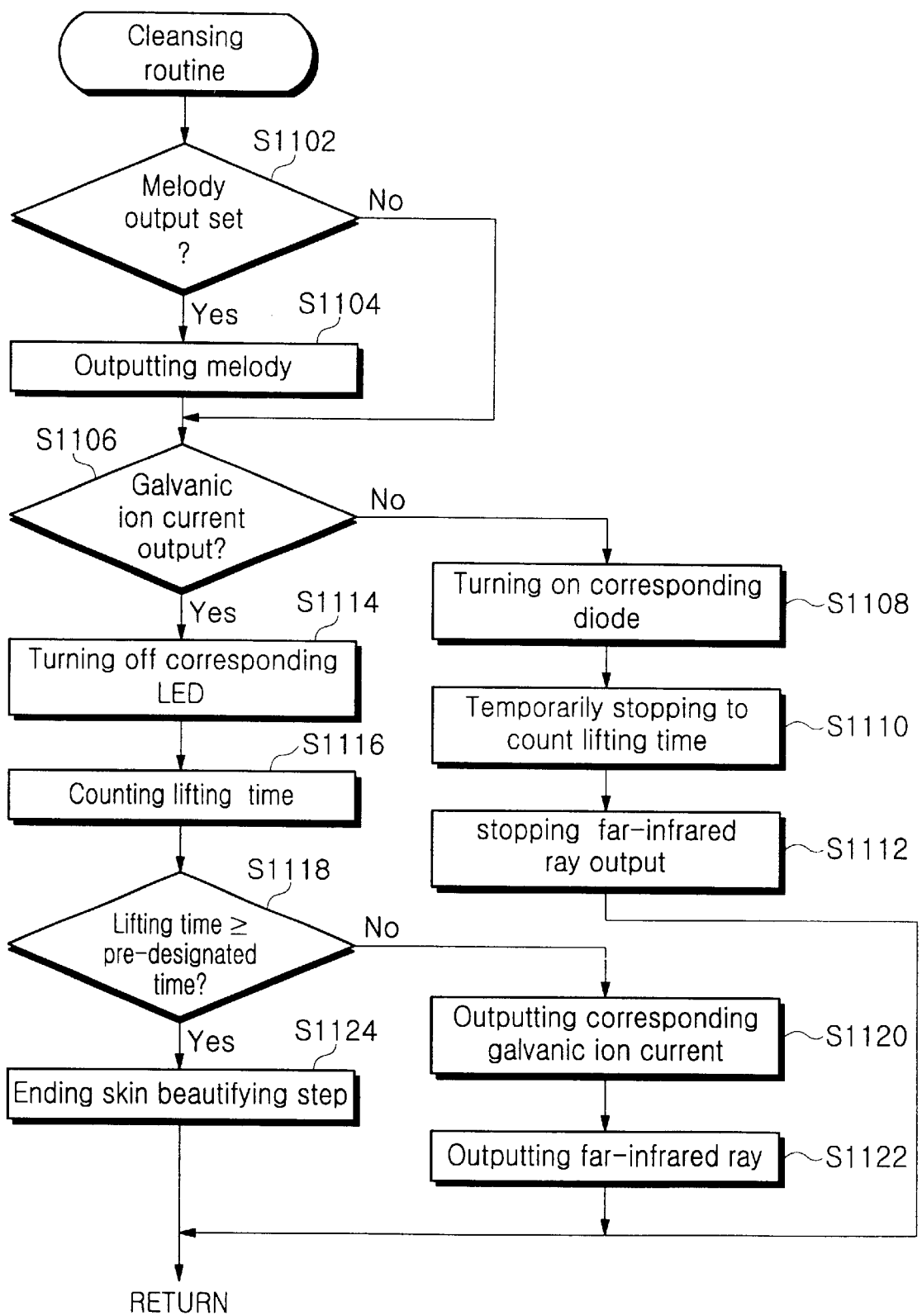
FIG. 11 is a flow chart showing the lifting routine of FIG. 7.

Referring to FIG. 11, the lifting routine mentioned in the step S718 of FIG. 7 first determines whether or not the melody output has been set (S1102).

When the melody output has been set from the determining step (S1102) of the melody output, the alarm/melody output part 240 outputs a melody by the control of the microcomputer 200 (S1004). Thereafter, it is determined whether or not the galvanic ion current is output onto the user's face skin (S1106).

When the galvanic ion current is not output onto the user's face skin in the galvanic ion current output determining step S1106, the corresponding LED 112 is turned on (S1108) and whereby it is displayed that the lifting step is stopped and simultaneously it is displayed that the galvanic ion current is not output onto the user's face skin.

Afterwards, it is temporarily stopped to count a time taken in performing the lifting step in the step S1110 and to output far-infrared ray in the step S1112.

When the galvanic ion current is output onto the user's face skin in the step S1106, the microcomputer 200 turns off the corresponding LED 112 in the step S1114, thereby displaying performing the lifting step. In the step S1116, the microcomputer 200 counts a time taken in performing the lifting step and thereafter determines whether or not the counting time is more than the pre-designated time in the step S1118.

When the counting time of the lifting step is less than the pre-designated time in the step S1118, the microcomputer 200 outputs a galvanic ion current corresponding to the lifting step in the step S1120

As shown in FIG. 12D, the galvanic ion current corresponding to the lifting step in the step S1120 has a discrete positive and negative galvanic ion current in which the pulse width is decreasingly varied for one period of 2T. The discrete positive and negative alternating galvanic ion current has a frequency which is varied within a range of 0.5–5 Hz.

Thereafter, a far-infrared ray is output by controlling the far-infrared ray generating part 290 according to user's selection level of strong or weak level (S1122).

Thus, the lifting step outputs a galvanic ion current of a discrete tooth wave in which a frequency is varied in a frequency range of 0.5–5 Hz and outputs a far-infrared ray, whereby pores of the face skin is expanded or reduced, resulting in allowing the face skin to be resilient and bright.

In this state, when the performing time of the lifting step which is set in the step S1118 elapses, the microcomputer 200 ends all the beautifying steps.

The vibration function follows a noise during the performing of the cleansing step, the massage step, and the nutrition supply step. Accordingly, the vibration level is controlled according to user's selection. In other words, the vibration control function is provided for users that dislike a noise generation due to the driving of the motor.

Moreover, the melody output level setting function is provided for users that dislike the noise generation but need the vibration function.

Meanwhile, although the present embodiments show and describe to generate the vibration by continuously driving the motor in the cleansing step, massage step, and nutrition supply step in which the vibration generation function has been step, the present invention does not restricted thereto. A rhythmical vibration can be also generated by periodically stopping the motor.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A control method of a portable beautifying apparatus comprising:

a first step performing an initializing operation by turning on an electric power and determining whether or not a key signal is input;

a second step setting a skin beautifying step according to the key signal when the key signal is input in the first step and performing skin measurement;

a third step performing the skin measurement when the key signal is not input in the first step but the skin measurement is being performed, and determining a present beautifying step when the skin measurement is not being performed and performing a beautifying operation;

a fourth step alternatively outputting a discrete positive galvanic ion current having a first frequency and a consecutive positive galvanic ion current for a first time period when the beautifying step determined in the third step is a cleansing step, and simultaneously setting a massage step after outputting far-infrared ray and vibration operations;

a fifth step repeatedly outputting a discrete positive galvanic ion current, a discrete negative galvanic ion current, and a positive and negative alternating galvanic current for a second time period each of which has a second frequency when the present beautifying step determined in the third step is the massage step, and setting a nutrition supply step after outputting far-infrared ray and vibration operations;

a sixth step repeatedly outputting a discrete negative galvanic ion current having a third frequency and a consecutive negative galvanic ion current for a third time period when the present beautifying step determined in the third step is the nutrition supply step, and setting a lifting step after outputting far-infrared ray and vibration operations; and a seventh step repeatedly outputting a positive and negative alternating galvanic ion current varied for a selected time within a set frequency range when the present beautifying step determined in the sixth step is the lifting step, and ending the skin beautifying steps after outputting far-infrared ray and vibration operations.

2. The method of claim 1, wherein the skin measurement is displayed by determining a skin state from a galvanic ion current level flowing onto user's face skin.

3. The method of claim 1, wherein the vibration is output or stopped depending on user's selection.

4. The method of claim 1, wherein the galvanic ion current, the far-infrared ray, and the vibration outputs are output to strong or weak level depending on user's set condition.

5. The method of claim 1, wherein the first, second, third galvanic ion current has an output frequency of approximately 2–10 Hz.

6. The method of claim 1, wherein the galvanic ion current has a period of 2–3 seconds.

7. The method of claim 1, wherein the set frequency range of the seventh step is in a range of 0.5–5 Hz.

8. The method of claim 1, further comprising a step of preventing a battery from being over-discharged by turning off the power when the battery's power is less than a pre-designated voltage.

9. The method of claim 1, wherein the skin beautifying step counts a time in which the galvanic ion current flows onto the user's face skin and is performed when the counting time is more than a pre-designated time.

* * * * *